(12) United States Patent
Fung (10) Patent No.: US 9,150,988 B2
(45) Date of Patent: Oct. 6, 2015

(54) METHOD FOR MAKING A FIBROUS ABSORBENT MATERIAL

(71) Applicant: JOHNSON & JOHNSON CONSUMER INC., Skillman, NJ (US)

(72) Inventor: Paul Y. Fung, New York, NY (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 14/187,797

(22) Filed: Feb. 24, 2014

(65) Prior Publication Data

US 2015/0052714 A1 Feb. 26, 2015

Related U.S. Application Data

(63) Continuation of application No. 13/236,788, filed on Sep. 20, 2011, now Pat. No. 8,695,185.

(51) Int. Cl.

| | |
|---|---|
| *D04H 1/46* | (2012.01) |
| *D04H 18/02* | (2012.01) |
| *D04H 1/4382* | (2012.01) |
| *D04H 1/58* | (2012.01) |
| *A61F 13/15* | (2006.01) |
| *D04H 1/4266* | (2012.01) |

(52) U.S. Cl.
CPC ............ *D04H 1/46* (2013.01); *A61F 13/15642* (2013.01); *D04H 1/4266* (2013.01); *D04H 1/4382* (2013.01); *D04H 1/58* (2013.01); *D04H 18/02* (2013.01); *D10B 2401/022* (2013.01); *D10B 2509/026* (2013.01)

(58) Field of Classification Search
CPC ......... D04H 1/46; D04H 3/102; D04H 3/105; D04H 5/102; D04H 18/02
USPC ...................... 28/107, 109–115; 442/403, 405
See application file for complete search history.

(56) References Cited

U.S. PATENT DOCUMENTS

| | | | |
|---|---|---|---|
| 3,085,309 | A | 4/1963 | Olson |
| 3,122,140 | A | 2/1964 | Crowe, Jr. |
| 3,243,861 | A | 4/1966 | Kumin, et al. |
| 3,511,740 | A | 5/1970 | Sanders |
| 3,545,442 | A | 12/1970 | Ward |
| 3,811,445 | A | 5/1974 | Dostal |
| 4,826,498 | A | 5/1989 | Koczab |
| 4,847,140 | A * | 7/1989 | Jaskowski ..................... 428/220 |
| 5,256,477 | A | 10/1993 | Mahoney |
| 5,470,326 | A | 11/1995 | Dabi et al. |
| 5,820,615 | A | 10/1998 | Koczab |
| 5,879,487 | A | 3/1999 | Ravella |
| 5,928,973 | A | 7/1999 | Daniel et al. |
| 6,781,027 | B2 | 8/2004 | Fenwick et al. |
| 7,516,525 | B2 | 4/2009 | Ramkumar |
| 2008/0313873 | A1 | 12/2008 | Link et al. |
| 2009/0000643 | A1 | 1/2009 | Schaadt et al. |
| 2011/0150558 | A1 | 6/2011 | Bissah et al. |

FOREIGN PATENT DOCUMENTS

EP          0525676          2/1993

* cited by examiner

*Primary Examiner* — Amy Vanatta (57) ABSTRACT

An absorbent material including a fibrous material having a plurality of individual fibers forming a fiber matrix, a plurality of absorbent fibers, wherein the plurality of absorbent fibers are impregnated within the fiber matrix by means of a needlepunch process.

1 Claim, 8 Drawing Sheets

METHOD FOR MAKING A FIBROUS ABSORBENT MATERIAL

CROSS REFERENCE TO RELATED APPLICATION

The present application is a continuation application of U.S. patent application Ser. No. 13/236,788 filed Sep. 20, 2011, now U.S. Pat. No. 8,695,185, the entirety of which application is hereby incorporated by reference herein as if fully set forth herein.

FIELD OF THE INVENTION

The present invention generally relates to an absorbent material and a method for making the same. More particularly, the present invention relates to an absorbent material for use in disposable sanitary absorbent products such as sanitary napkins, pantiliners, tampons, diapers, adult incontinence products, and the like.

BACKGROUND OF THE INVENTION

Lofty, resilient, non-woven webs, that is nonwoven webs that have a high degree of loft and the tendency to retain such loft, are well known. In addition, it is well known that such lofty, resilient, non-woven webs may be used in disposable sanitary products such as sanitary napkins, pantiliners, tampons, diapers, adult incontinence products, and the like. A perceived benefit of such lofty, resilient, non-woven webs is that such materials may deliver enhanced comfort to a user of such disposable sanitary products since the lofty, resilient, nonwoven webs may tend to conform to, and move with, the user's body during use.

A problem with lofty, resilient, nonwoven webs is that due to the loft of such materials (i.e. their low density) such webs are not particularly absorbent. In addition, such materials may exhibit poor rewet properties. That is, such materials may release or "wet back" fluid when subjected to an external pressure.

In view of the foregoing there is a need for a lofty, resilient, non-woven web that also provides superior fluid handling characteristics.

SUMMARY OF THE INVENTION

In view of the foregoing, the present invention provides, a method for making an absorbent material including the steps of providing a fibrous material including a plurality of individual fibers forming a fiber matrix, depositing a plurality of absorbent fibers on a top surface of the fibrous material, and impregnating the plurality of absorbent fibers into the fiber matrix by means of a needlepunch process.

BRIEF DESCRIPTION OF THE DRAWINGS

Examples of embodiments of the present invention will now be described with reference to the drawings, in which.

DETAILED DESCRIPTION OF THE INVENTION

Throughout the present specification, the same or similar reference numbers have been used to identify the same or similar elements of the various embodiments of the present invention described herein.

Figure 1:
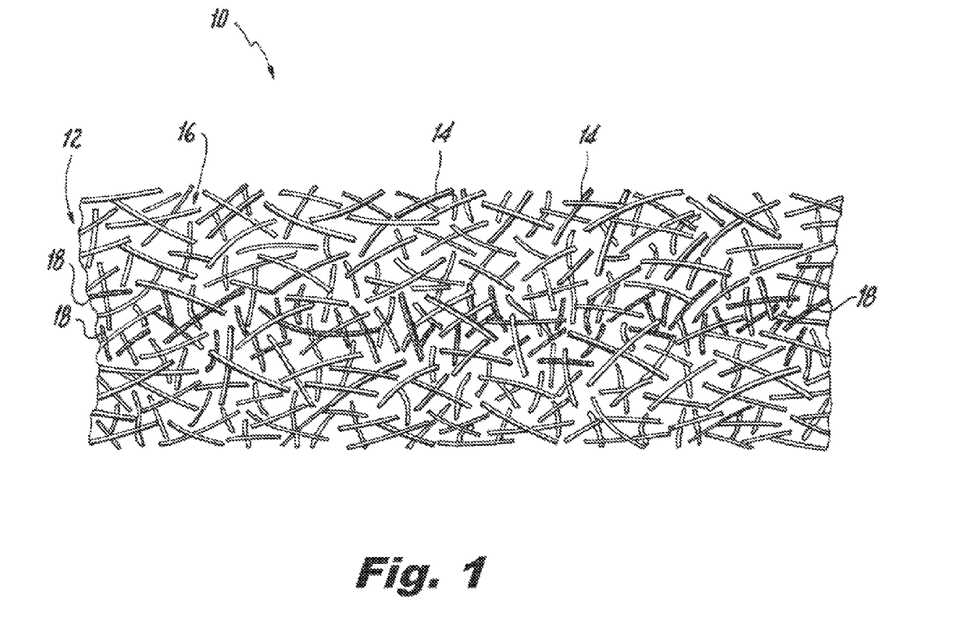
FIG. 1 is a sectional schematic view of an absorbent material according to a first embodiment of the present invention.

Reference is made to FIG. 1 which illustrates a sectional schematic view of an absorbent material 10 according to a first embodiment of the present invention. As shown in FIG. 1, the absorbent material 10 is formed from a fibrous material 12 including a plurality of individual fibers 14 that form a fiber matrix 16. The absorbent material 10 further includes a plurality of absorbent fibers 18. As shown, the absorbent fibers 18 are impregnated within the fiber matrix 16.

The fibrous material 12 is preferably a fibrous nonwoven material made by a known nonwoven manufacturing technique such as an airlaid process, a card and bind process or a resin and adhesive bond process. Preferably the nonwoven material is a "high loft" nonwoven. Specifically, the nonwoven preferably has a density lower than 0.05 g/cc, and preferably between about 0.01 g/cc and 0.03 g/cc, prior to the impregnation of the nonwoven with the absorbent fibers 18. The individual fibers 14 forming the fibrous nonwoven material may be selected from fibers including synthetic, nonabsorbent fibers that may or may not be wettable, for example hydrophilic fibers, hydrophobic fibers, and combinations thereof. Specific fiber types include, but are not limited to, polyester, nylon, co-polyester, polyethylene, polypropylene, and polylactic acid. Of course the fibrous nonwoven material may be formed from a single nonabsorbent fiber type listed above or alternatively may be formed from a mixture of the fiber types listed above. The surface of nonabsorbent fibers 14 forming the fibrous material 12 may be rendered wettable by treating such fibers with a suitable surface treatment, such a surfactant or like.

Each of the fibers 14 forming the fibrous nonwoven material preferably has a fiber diameter within the range of 11 μm and 100 μm. The fibrous material 12 preferably further includes a binder material, such as a latex binder. The binder material is preferably present in the fibrous material 12 in an amount between about 30% by weight to about 50% by weight.

The absorbent fibers 18 are preferably selected from cellulosic fiber types, such as, but not limited to, hard wood pulp, soft wood pulp, rayon, and cotton. The absorbent material 10 may include a single absorbent fiber type of those listed above or in the alternative may include multiple fiber types of those listed above (i.e. a mixture of absorbent fibers). Each of the absorbent fibers 18 preferably has fiber diameter within the range of 10 μm and 40 μm.

The individual fibers 14 forming the fibrous material 12 and the absorbent fibers 18 are selected such that each of the individual fibers 14 has a fiber diameter that is at least 1 μm greater than a fiber diameter of each of the absorbent fibers 18.

As will be discussed in greater detail below, the absorbent fibers 18 are impregnated within the fiber matrix 16 by means of a needlepunch process according to the present invention. The needlepunch process according to the present invention, described in detail below, allows the absorbent fibers 18 to be impregnated within the fiber matrix 16 without the fibrous material 12 losing its high loft properties. Specifically, the density of fibrous material 12 prior to being impregnated with the absorbent fibers 18 is preferably within the range of 0.01 g/cc and 0.03 g/cc.

The fibrous material 12 preferably has a thickness in the range of about 1.5 mm to about 5 mm prior to impregnation of the fibrous material 12 with the absorbent fibers 18. After impregnation of the fibrous material 12 with the absorbent fibers 18 the absorbent material 10 retains substantially the same thickness as the original fibrous material. Specifically, a percent change between the thickness of the fibrous material 12 prior to the plurality of absorbent fibers 18 being impregnated therein and a thickness of the absorbent material 10 after the absorbent fibers 18 have been impregnated within the fibrous material 12 is preferably less than 50%, more preferably less than 30% and most preferably less than 15%. This relatively small change in thickness reflects that the absorbent material 10 retains the high loft properties of the fibrous material 12 while at the same time delivers superior fluid handling capabilities. The percent change in thickness is calculated as follows:

$$\% \Delta T = (Ti - Tf)/Ti;\ where$$

Ti=Initial Thickness of Fibrous Material 12
Tf=Final Thickness of Absorbent Material 10

Figure 2:
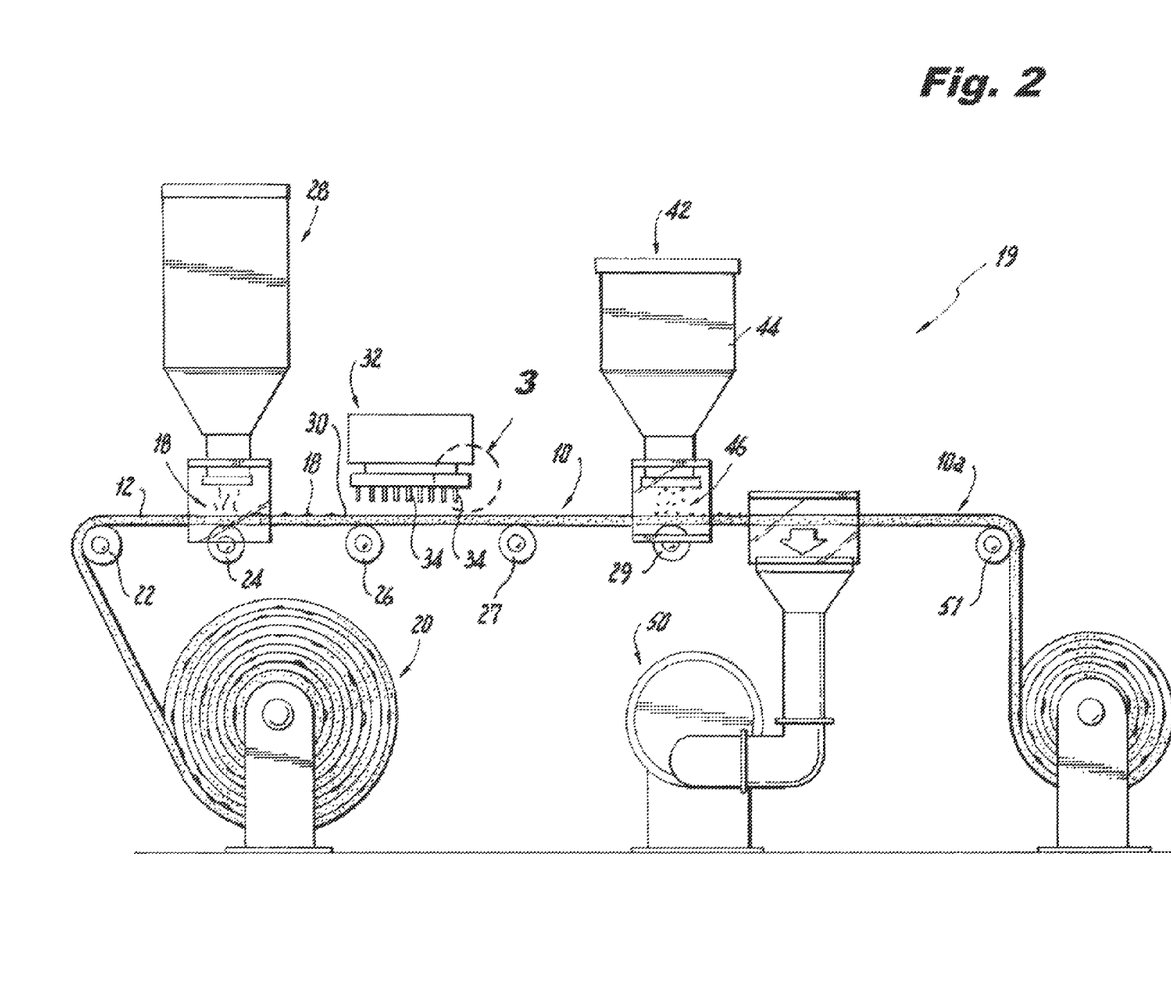
FIG. 2 is a schematic view of an apparatus for making the absorbent material shown in FIG. 1.

A method of making the absorbent material 10 will now be described with reference to FIG. 2 which depicts a schematic representation of an apparatus 19 for making the absorbent material 10. As shown in FIG. 2, a web of fibrous material 12 is fed from a supply roll 20 and conveyed in a machine direction by a plurality of rolls 22, 24 and 26. A gravity fed hopper 28, or the like, is utilized to apply a selected amount of absorbent fibers 18 to a top surface 30 of the fibrous material 12. Thereafter, the fibrous material 12 is further conveyed in a machine direction and passed through a conventional needlepunch apparatus 32 of the type known to those of skill in the art. In the method according to the present invention, the needlepunch apparatus 32 functions to impregnate the absorbent fibers 18 within the fibrous material 12 by means of a plurality of needles 34.

Figure 3:
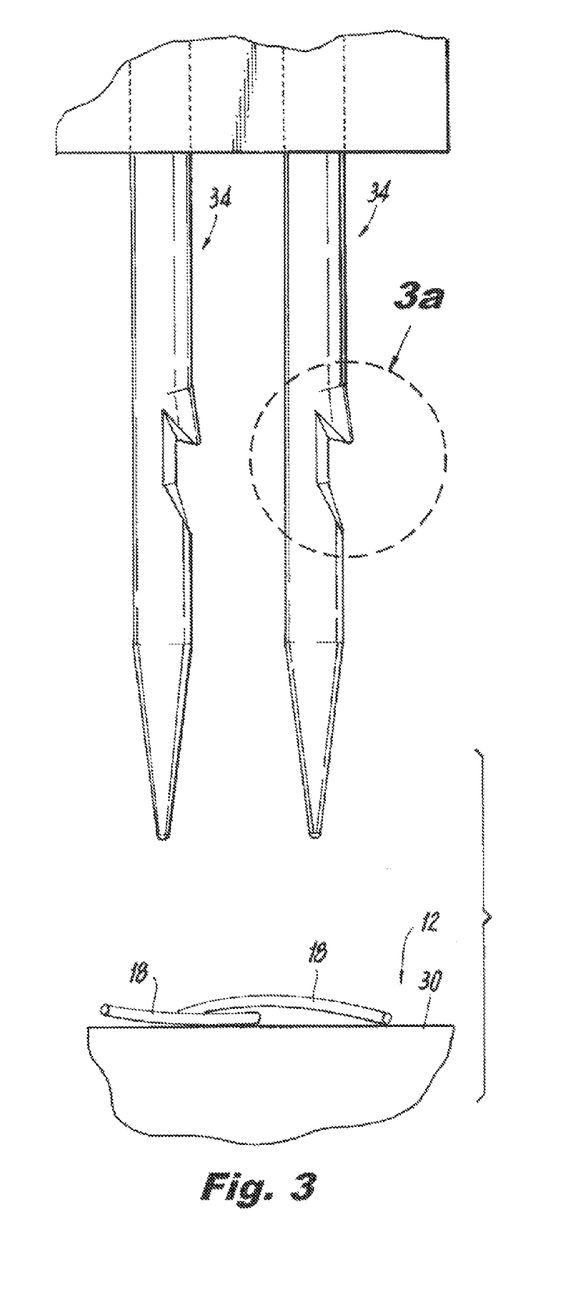
FIG. 3 is a schematic view of the encircled portion of the apparatus shown in FIG. 2 depicting a needle employed in the apparatus, a top surface of a substrate, and absorbent fibers arranged on the top surface of the substrate.
Figure 3A:
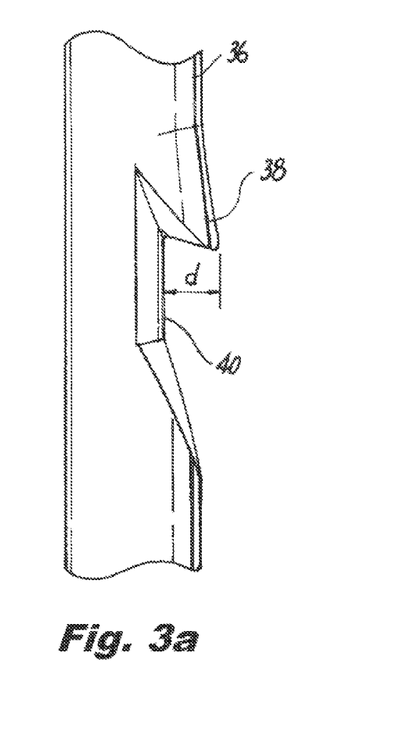
FIG. 3a is a detailed view of the encircled portion of the needle shown in FIG. 3.
Figure 3B:
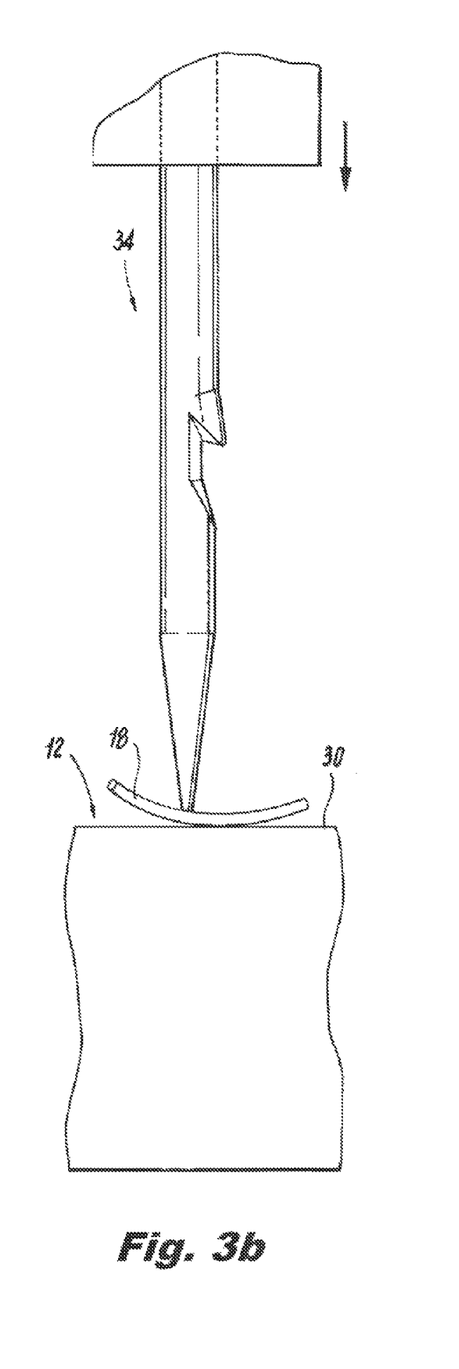
FIG. 3b-3e depict the manner in which the needle impregnates the absorbent fiber within the substrate.
Figure 3C:
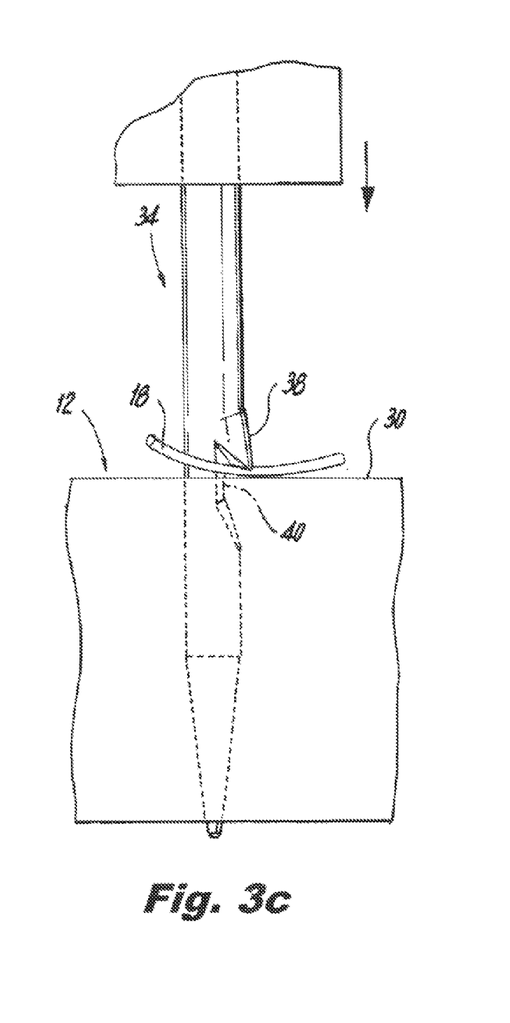
Figure 3D:
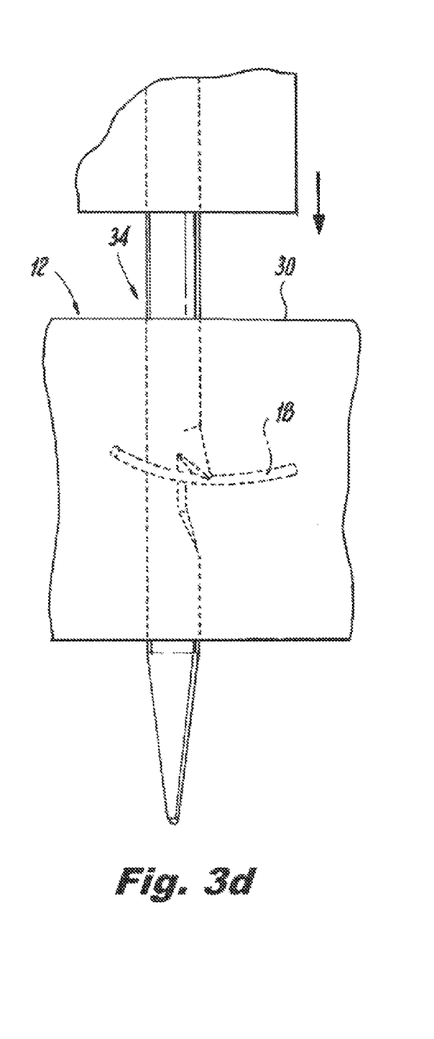
Figure 3E:
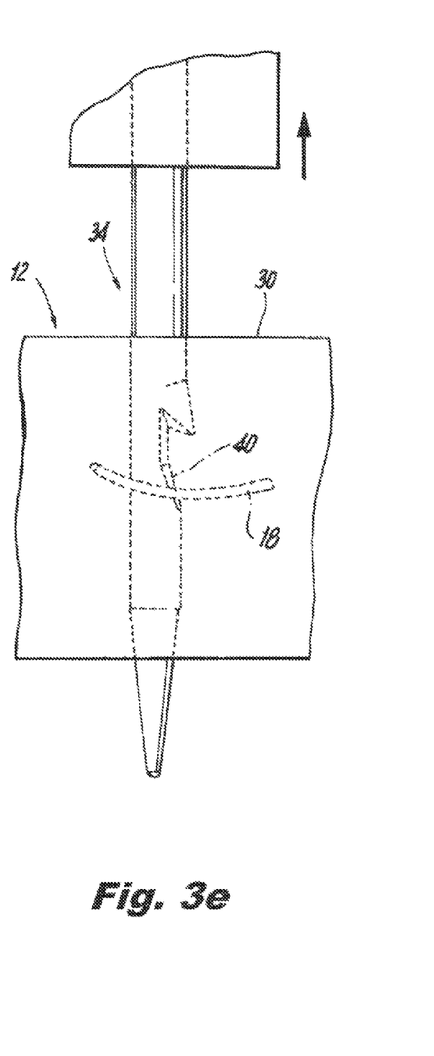

As is known to those of skill in the art, a conventional needlepunch apparatus includes a plurality of needles that are normally adapted to mechanically orient and interlock the fibers of a spunbonded or carded web. In the method according to the present invention, the needles 34 of the needlepunch apparatus 32 are used to impregnate absorbent fibers 18 within the fibrous material 12. A needle 34 suitable for use in the method according to the present invention is depicted in FIG. 3 and FIG. 3*a*. As shown in FIG. 3*a*, the needle 34 generally includes a blade 36, a barb 38, and a throat section 40. The total barb depth of the barb 38 is indicated by letter "d" in the FIG. 3*a*.

For purposes of the present invention, it is critical that the barb depth "d" is selected such that a radius of each of the absorbent fibers 18 is smaller than the barb depth "d". The radius of each absorbent fiber 18 is at least 0.5 μm smaller, for example 1 μm smaller than the barb depth. In addition the barb depth "d" should be selected such that each of the individual fibers 14 of the fibrous material 12 has a radius that is larger than the barb depth "d". The radius of each individual fiber 14 of the fibrous material 12 is at least 0.5 μm larger, for example 1 μm larger than the barb depth. If you have a multiple denier fibrous material 12, the diameter of the smallest diameter fiber 14 must be larger than the diameter of each of the absorbent fibers 18.

By selecting barb depth "d" as described above, the plurality of needles 34 in the needlepunch apparatus effectively grasp the absorbent fibers 18 and thus can impregnate such absorbent fibers 18 within the fibrous material 12, as shown in FIGS. 3*b*-3*e*. On the other hand, the plurality of needles 34 will not grasp the individual fibers 14 of the fibrous material 12 and thus will not destroy the "high loft" properties of the fibrous material 12. In this manner the final absorbent material 10 is provided with superior fluid handling properties while still retaining the high loft properties of the fibrous material 12. Needles particularly useful in the present method are commercially available from the Foster Needle Co., Inc., Manatowoc, Wis., under product designation "The Foster Formed Barb".

Referring again to FIG. 2, after the fibrous 12 has been impregnated with the absorbent fibers 18 the resultant absorbent material 10 is further conveyed in a machine directly by rolls 28 and 30. At this point in the process the absorbent material 10 may be arranged in a rolled form for storage or may be further conveyed for incorporation into disposable sanitary absorbent products such as a sanitary napkin, pantiliner, tampons, diaper, adult incontinence product, or the like.

Figure 4:
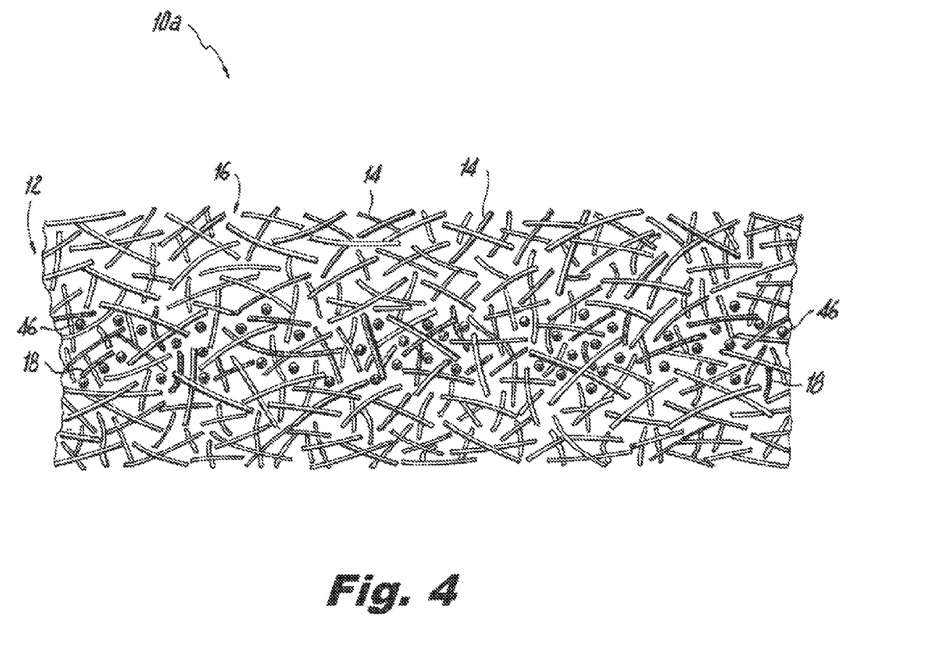
FIG. 4 is a sectional schematic view of an absorbent material according to a second embodiment of the present invention.

Alternatively, as shown in FIG. 2, the fibrous material 12 may be further conveyed to a superabsorbent application station 42. The superabsorbent application station 42 comprises a gravity fed hopper 44 structured and arranged to apply a selected amount of superabsorbent polymer material 46 to a top surface 30 of the fibrous material 12. Of course, any suitable means known to those of skill in the art, such as a pressure fed nozzle or the like, may be used to apply the superabsorbent polymer material 46 to the top surface 30 of the fibrous material 12. After the superabsorbent polymer material 46 is applied to the top surface 30 of the fibrous material 12, the fibrous material 12 is conveyed over a vacuum 50 that functions to draw the superabsorbent polymer material 46 into the fiber matrix 16 of the fibrous material 12. The resultant absorbent material 10*a*, an absorbent material according to a second embodiment of the invention, is shown in FIG. 4. As shown, the superabsorbent polymer 46 has been drawn into the fiber matrix 16 of the fibrous material 12 and functions to further enhance the fluid handling capabilities of the absorbent material 10*a*.

For the purposes of the present invention, the term "superabsorbent polymer" (or "SAP") refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. Preferred superabsorbent polymer particles for use in the present invention are crosslinked polyacrylates, such as the product offered by Sumitomo Seika Chemicals Co., Ltd. of Osaka, Japan, under the designation of SA70.

Referring again to FIG. 2, after the absorbent material 10*a* is conveyed past the vacuum 50 the absorbent material 10*a* may be further conveyed in a machine direction by roll 51 and arranged in a rolled form for storage or may be further conveyed for incorporation into a disposable sanitary absorbent products such as a sanitary napkin, pantiliner, tampons, diaper, adult incontinence product, or the like.

Figure 5:
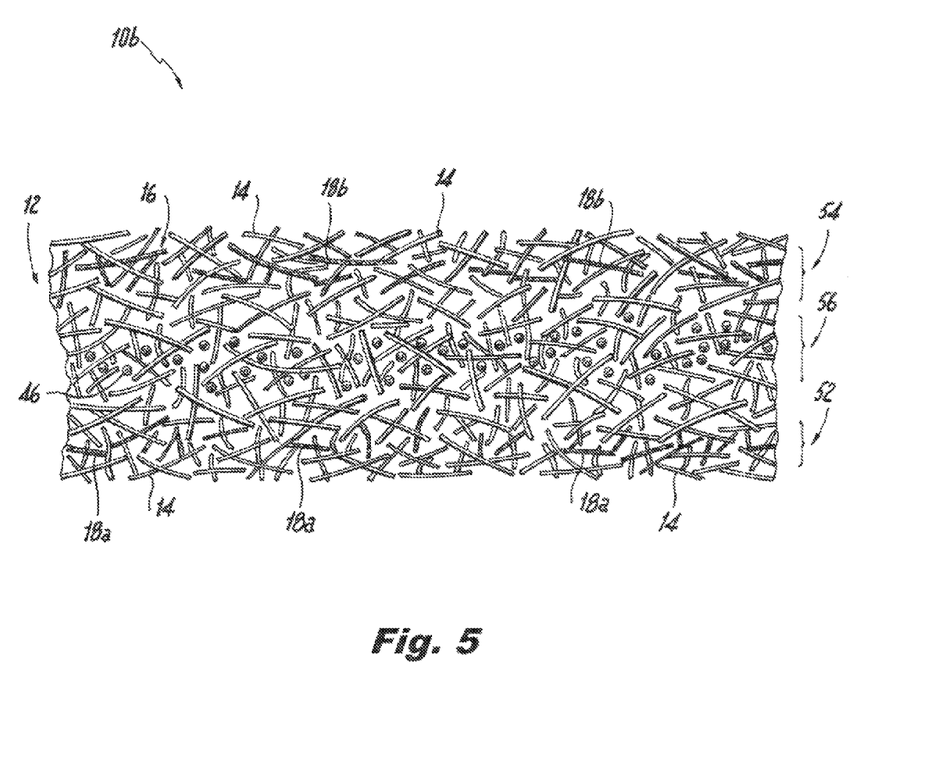
FIG. 5 is a sectional schematic view of an absorbent material according to a third embodiment of the present invention.

Reference is made to FIG. 5 which illustrates a sectional schematic view of an absorbent material 10b according to a third embodiment of present invention. As shown, the absorbent material 10b is formed from a fibrous material 12 including a plurality of individual fibers 14 that form a fiber matrix 16. The absorbent material 10b further includes a first plurality of absorbent fibers 18a arranged in a first layer 52 and a second plurality of absorbent fibers 18b arranged in a second layer 54. The absorbent fibers 18a and 18b may comprise the same fibers as those absorbent fibers 18 described above with regard to the first embodiment of the present invention. The absorbent fibers 18a and 18b may be the same fiber type or may be different fibers types (i.e. a mixture of fibers). In addition, a first absorbent fiber mixture (or individual fiber) may be employed in the first plurality of fibers 18a and different absorbent fiber mixture (or individual fiber) may be employed in the second plurality of fibers 18b.

The individual fibers 14 may be the same as the fibers 14 described above with regard to the first embodiment. In addition the individual fibers 14 may be the same fiber type (i.e. a single fiber type) or different fiber types (i.e. a mixture of fibers).

In the particular embodiment of the invention shown in FIG. 5, the first layer 52 is arranged in spaced relationship to the second layer 54. The absorbent material 10b may optionally further include superabsorbent polymer material 46 dispersed within the fiber matrix 16 of the fibrous material 12. In the particular embodiment of the invention shown in FIG. 5, the superabsorbent 46 is arranged in a layer 56 between the first layer 52 and second layer 54 of the absorbent fibers 18a and 18b. Of course the superabsorbent polymer material 46 may be omitted from the absorbent material 10b if desired.

Figure 6:
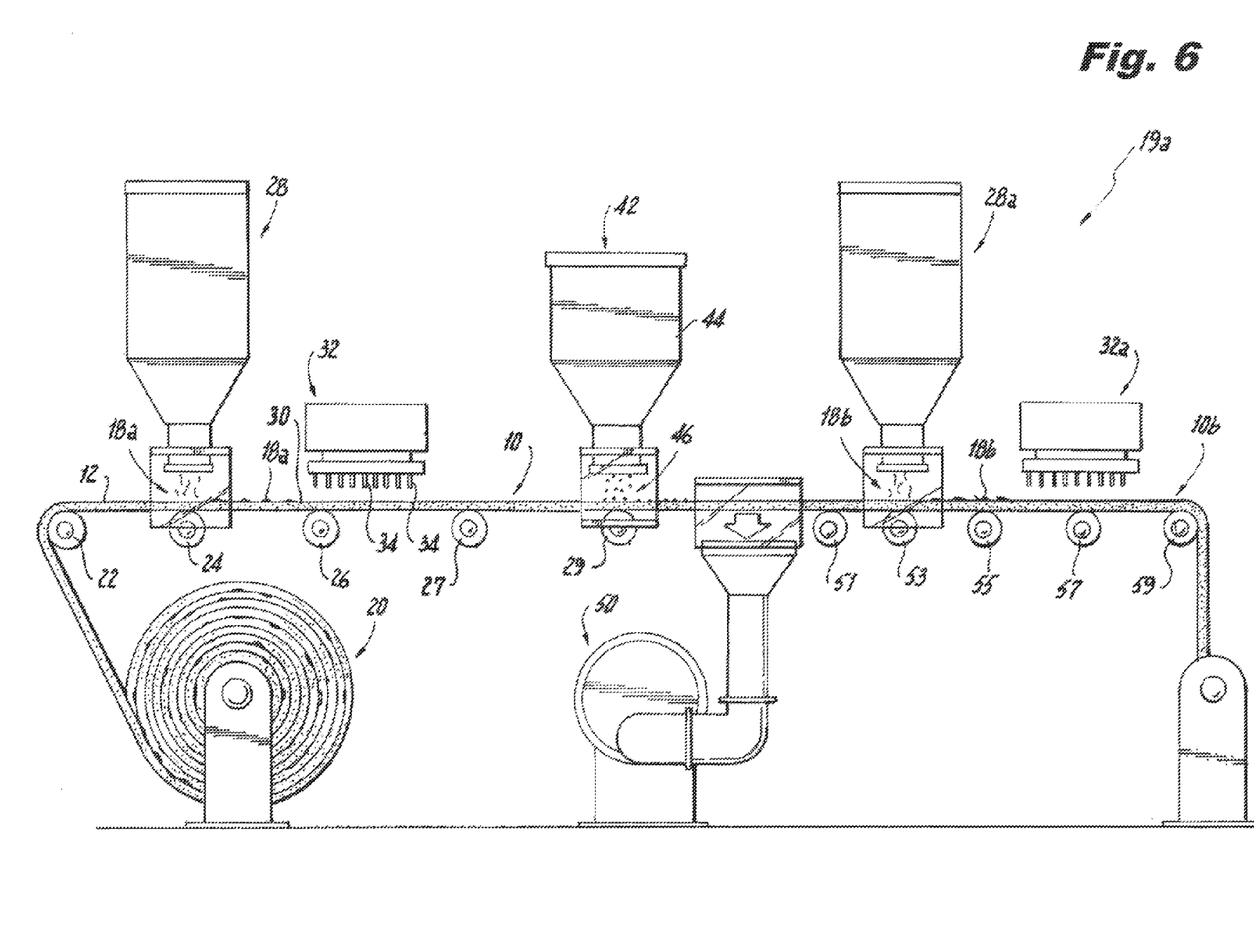
FIG. 6 is a schematic view of an apparatus for making the absorbent material shown in FIG. 5.

A method of making the absorbent material 10b will now be described with reference to FIG. 6 which depicts a schematic representation of an apparatus 19a for making the absorbent material 10b. As shown in FIG. 6, a web of fibrous material 12 is fed from a supply roll 20 and conveyed in a machine direction by a plurality of rolls 22, 24 and 26. A gravity fed hopper 28, or the like, is utilized to apply a selected amount of absorbent fibers 18a to a top surface 30 of the fibrous material 12. Thereafter, the fibrous material 12 is further conveyed in a machine direction and passed through a needlepunch apparatus 32 for impregnating the absorbent fibers 18a within the fibrous material 12.

Thereafter the fibrous material 12 is further conveyed to a superabsorbent application station 42. The superabsorbent application station 42 comprises a gravity fed hopper 44 structured and arranged to apply a selected amount of superabsorbent polymer material 46 to a top surface 30 of the fibrous material 12. Of course, any suitable means known to those of skill in the art, such as a pressure fed nozzle or the like, may be used to apply the superabsorbent polymer material 46 to the top surface 30 of the fibrous material 12. After the superabsorbent polymer material 46 is applied to the top surface 30 of the fibrous material 12 the fibrous material 12 is conveyed over a vacuum 50 that functions to draw the superabsorbent polymer material 46 into the fiber matrix 16 of the fibrous material 12. Of course, if the inclusion of superabsorbent polymer material 46 is not desired in the absorbent material 10b, the superabsorbent application and vacuum step described may be omitted from the described method.

After the fibrous material 12 is conveyed past the vacuum 50, the fibrous material 12 is conveyed by rolls 51 and 53 to a second gravity fed hopper 28a, or the like, to apply a selected amount of absorbent fibers 18b to a top surface 30 of the fibrous material 12. Thereafter, the fibrous material 12 is further conveyed in a machine direction by rolls 55 and 57 and passed through a second needlepunch apparatus 32a for impregnating the absorbent fibers 18b within the fibrous material 12.

Referring again to FIG. 6, after the absorbent material 10b is conveyed past the needlepunch apparatus 32a the absorbent material 10b is further conveyed in a machine direction by roll 59 and then may be arranged in a rolled form for storage or may be further conveyed for incorporation into a disposable sanitary absorbent products such as a sanitary napkin, pantiliner, tampons, diaper, adult incontinence product, or the like.

EXAMPLES

Specific examples of the present invention are described below.

Inventive Example #1

An absorbent material as described above with reference to FIGS. 1 and 2 is made as follows. The fibrous material is a fibrous nonwoven made by a card and bind process having a basis weight of 68 gsm, formed from 100% polyester fibers (6 denier), and having a thickness of 3 mm. Given that the density of polyester is 1.38 g/cc, a 6 denier fiber has a nominal diameter of 25 μm (denier=density*0.0283 $r^2$). The fibrous material includes a latex binder present in the amount of 40% by weight. A fibrous nonwoven material of this type is commercially available from Kem-Wove, Inc., Charlotte, N.C. under product code SCN09-038. The absorbent fibers comprise 100% viscose rayon having a denier of 4. Rayon has a density of 1.5 g/cc thus the absorbent fibers have a fiber diameter of 19 μm. 150 gsm (g/$m^2$) of the rayon fibers are applied to a top surface of the fibrous nonwoven material and impregnated within the material to a depth of 2.5 mm by means of the needlepunch process described above with reference to FIG. 2. The needles used in the needlepunch process have a barb depth "d" of 12 μm. The final absorbent material has a thickness of 2.7 mm.

Inventive Example #2

An absorbent material as described above with referenced to FIGS. 5 and 6 is made as follows. The fibrous material is a fibrous card and bind nonwoven material having a basis weight of 68 gsm, formed from 100% polyester fibers (6 denier), and having a thickness of 3 mm. Given that the density of polyester is 1.38 g/cc, a 6 denier fiber has a nominal diameter of 25 μm (denier=density*0.0283 $r^2$). The fibrous material includes a latex binder present in the amount of 40% by weight. A fibrous nonwoven material of this type is commercially available from Kem-Wove, Inc., Charlotte, N.C. under product code SCN09-038. The first plurality of absorbent fibers comprises 100% viscose rayon having a denier of 4. Rayon has a density of 1.5 g/cc thus the absorbent fibers have a fiber diameter of 19 μm. 75 gsm of the rayon fibers are applied to a top surface of the fibrous nonwoven material and impregnated within the material to a depth between 4.0 mm and 5.0 mm by means of a first needlepunch apparatus. The needles used in the needlepunch process have a barb depth "d" of 12 μm. Thereafter, the fibrous material is conveyed to a superabsorbent application station. 40 gsm of superabsorbent (SA70 commercially available from Sumitomo Seika Chemicals Co., Ltd. Of Osaka, Japan) is applied to a top surface of the fibrous material via a gravity fed hopper. The superabsorbent is drawn into the fibrous material at a depth between 3.0 mm and 4.0 mm by means of a vacuum. Thereafter, the fibrous material 12 is conveyed to a second gravity fed hopper to apply a selected amount of a second plurality of absorbent fibers to a top surface of the fibrous material. The second plurality of absorbent fibers comprises 100% viscose rayon having a denier of 4. Rayon has a density of 1.5 g/cc thus the absorbent fibers have a fiber diameter of 19 μm. 75 gsm of the rayon fibers are applied to a top surface of the fibrous nonwoven material and impregnated within the material to a depth between 1.0 mm and 3.0 mm by means of a second needlepunch apparatus. The needles used in the second needlepunch process have a barb depth "d" of 12 μm. The final absorbent material has a thickness of 2.5 mm.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of the invention.

I claim:

1. A method for making an absorbent material comprising the steps of:

providing a fibrous material including a plurality of individual fibers forming a fiber matrix, the fibrous material having a thickness;

depositing a plurality of absorbent fibers on a top surface of the fibrous material; and impregnating the plurality of absorbent fibers into the fiber matrix by means of a needlepunch process, the needlepunch process carried out by means of a plurality of individual pins adapted to impregnate the absorbent fibers within the fiber matrix such that after impregnating the plurality of absorbent fibers into the fiber matrix, the absorbent material retains substantially the same thickness as the fibrous material prior to the impregnation of the fiber matrix, wherein each of the plurality of individual fibers has a fiber diameter within the range of between about 11 μm and 100 μm and at least 1 μm greater than a fiber diameter of each of the absorbent fibers and wherein each of the plurality of absorbent fibers has a fiber diameter within the range of between about 10 μm and 40 μm and further wherein each of the plurality of pins includes a barb having a barb depth and wherein said barb depth is selected such that a fiber radius of each of the absorbent fibers is at least 0.5 μm smaller than the barb depth and the fiber radius of each of the individual fibers forming a fiber matrix is at least 0.5 μm greater than the barb depth.

* * * * *